United States Patent
Jefferson et al.

(10) Patent No.: US 10,583,116 B2
(45) Date of Patent: Mar. 10, 2020

(54) LOCAL DELIVERY OF CHOLESTEROL-LOWERING DRUGS TO TREAT AND PREVENT BACTERIAL VAGINOSIS

(71) Applicant: VIRGINIA COMMONWEALTH UNIVERSITY, Richmond, VA (US)

(72) Inventors: Kimberly K. Jefferson, Midlothian, VA (US); Abdallah A. Abdelmaksoud, Richmond, VA (US); Philippe H. Girerd, Midlothian, VA (US); Gregory Buck, Richmond, VA (US)

(73) Assignee: VIRGINIA COMMONWEALTH UNIVERSITY, Richmond, VA (US)

( * ) Notice: Subject to any disclaimer, the term of this patent is extended or adjusted under 35 U.S.C. 154(b) by 0 days.

(21) Appl. No.: 16/327,702

(22) PCT Filed: Aug. 30, 2017

(86) PCT No.: PCT/US2017/049262
§ 371 (c)(1),
(2) Date: Feb. 22, 2019

(87) PCT Pub. No.: WO2018/044967
PCT Pub. Date: Mar. 8, 2018

(65) Prior Publication Data
US 2019/0192483 A1    Jun. 27, 2019

Related U.S. Application Data

(60) Provisional application No. 62/381,811, filed on Aug. 31, 2016.

(51) Int. Cl.
| | | |
|---|---|---|
| A61K 31/397 | (2006.01) | |
| A61K 31/366 | (2006.01) | |
| A61K 9/00 | (2006.01) | |
| A61P 31/04 | (2006.01) | |
| A61K 9/06 | (2006.01) | |
| A61K 45/06 | (2006.01) | |

(52) U.S. Cl.
CPC .......... *A61K 31/397* (2013.01); *A61K 9/0034* (2013.01); *A61K 9/0036* (2013.01); *A61K 9/06* (2013.01); *A61K 31/366* (2013.01); *A61K 45/06* (2013.01); *A61P 31/04* (2018.01)

(58) Field of Classification Search
CPC ........................ A61K 31/397; A61K 9/0034
See application file for complete search history.

(56) References Cited

U.S. PATENT DOCUMENTS

| | | | | |
|---|---|---|---|---|
| 2007/0231406 A1* | 10/2007 | Bucalo | ................ | A61K 9/0095 424/617 |
| 2012/0245132 A1* | 9/2012 | Zeng | ................ | A61K 9/0034 514/171 |
| 2015/0110898 A1* | 4/2015 | Gordon | ................ | A61K 31/198 424/659 |
| 2015/0320724 A1* | 11/2015 | Guan | ................ | A61K 45/06 424/464 |
| 2016/0220536 A1* | 8/2016 | Kohn | ................ | A61K 31/4164 |

OTHER PUBLICATIONS

Hennessy et al. Antimicrobial Agents and Chemotherapy, (Aug. 22, 2016), 60(9), p. 5111-5121.*
El-Refaie et al. J. Egypt Soc. Gynaecol. Obstet. (2011), 37(1), p. 583-587.*
Easmon et al., Genitourin Med, (1992) ;68:134-138).*
Hennesy et al. :"Statins as next generation anti-microbials: Is there potential for repurposing?," Antimicrobial Agents and Chemotherapy, Aug. 22, 2016, vol. 60, Iss. 9, pp. 5111.21.
Abdelmaksoud et al. "Association between statin use, the vaginal microbiome, and Gardnerella vaginalis vaginolysin-mediated cytotoxicity," PLoS One, Aug. 28, 2017, vol. 12, No. 8, pp. 1-17.

* cited by examiner

*Primary Examiner* — Yong L Chu
(74) *Attorney, Agent, or Firm* — W & C IP

(57) ABSTRACT

Methods of preventing and/or treating bacterial vaginosis are provided. The methods involve administration of cholesterol lowering drugs in combination with agents that reduce cholesterol absorption, and compositions for performing the methods.

15 Claims, 2 Drawing Sheets

Specification includes a Sequence Listing.

LOCAL DELIVERY OF CHOLESTEROL-LOWERING DRUGS TO TREAT AND PREVENT BACTERIAL VAGINOSIS

CROSS-REFERENCE TO RELATED APPLICATIONS

This application claims benefit of U.S. provisional patent application 62/381,811, filed Aug. 31, 2016, the complete contents of which is hereby incorporated by reference.

STATEMENT OF GOVERNMENT INTEREST

This invention was made with government support under P60 MD002256 awarded by National Institutes of Health (NIH). The government has certain rights in the invention.

SEQUENCE LISTING

This application includes as the Sequence Listing the complete contents of the accompanying text file "Sequence.txt", created Aug. 17, 2017, containing 65,536 bytes, hereby incorporated by reference.

BACKGROUND OF THE INVENTION

Field of the Invention

The invention generally relates to methods of preventing and/or treating bacterial vaginosis. In particular, the invention provides methods of preventing and/or treating bacterial vaginosis by local administration of cholesterol lowering drugs in combination with agents that reduce cholesterol absorption, as well as compositions for carrying out the methods.

Background

The healthy vaginal microbiome is generally predominated by lactobacilli, which produce lactic acid and other toxic products and are associated with reduced bacterial growth and limited bacterial diversity and bioburden. This was reflected in an analysis by Forney and Ravel (Microbial Ecology in States of Health and Disease: Workshop Summary (2014) Chapter: A11), which established five major groups of vaginal microbial communities using 16sRNA sequencing. The communities were designated "community state types" (CSTs) I-V. In this study, communities in CST I, which occurred in 26.2% of the women sampled, were dominated by *Lactobacillus crispatus*, while CST II (6.3%), CST III (34.1%), and CST V (5.3%) were dominated by *Lactobacillus gasseri*, *Lactobacillus iners*, and *Lactobacillus jensenii*, respectively. However, the remaining communities found in 27% of the women formed a large heterogeneous group (CST IV), and were typified by higher proportions of anaerobic and strictly anaerobic bacteria, including *Prevotella, Dialister, Atopobium, Gardnerella, Megasphaera, Peptoniphilus, Sneathia, Eggerthella, Aerococcus, Finegoldia*, and *Mobiluncus*.

It is known that when *Lactobacillus* numbers are low (such as in the CST IV group) the vaginal pH is typically higher and the vaginal microbiome can become dominated by bacterial taxa that are associated with bacterial vaginosis (BV), such as *Gardnerella vaginalis*. While symptoms of BV may be mild and in fact not reported or treated, this dysbiosis is nevertheless associated with an increased risk for preterm birth and the acquisition of sexually transmitted infections, including HIV.

African American (AA) women are more likely to exhibit CST IV whereas women of European ancestry (EA) are more likely to exhibit CST I (dominated by *L. crispatus*). AA women are also more than twice as likely to have BV relative to EA. This is important because AA are also more likely to give birth preterm (<37 weeks completed gestation), and three times more likely to experience very preterm birth (<32 weeks). This substantial health disparity is likely associated with differences in the vaginal microbiome.

Current therapeutic intervention for bacterial vaginosis is administration of an oral or vaginal antimicrobial agent such as metronidazole or clindamycin. However, antimicrobial therapy generally does not completely eradicate the bacterial species that cause BV (e.g. *G. vaginalis*). Evidence in the scientific literature suggests that this is due to formation of biofilms by the bacteria, which exhibit high-level tolerance to antimicrobial agents, so that once the antimicrobial therapy ceases, the bacteria that cause BV again begin to replicate. In fact, BV recurs in ~75% of cases. This is further complicated by the fact that antimicrobial therapy also kills healthy lactobacilli, which are needed to recolonize the vagina and prevent recurrences of BV.

There is a pressing need in the art for new therapies to manipulate the vaginal microbiome toward a healthy bacterial composition, thereby preventing and/or treating bacterial vaginosis, and/or lowering the risk of preterm and very preterm birth, and decreasing susceptibility to sexually transmitted diseases. Unfortunately, existing animal models are problematic as most of the bacterial taxa that make up the human vaginal microbiome do not colonize animals readily. Thus, other means must be utilized to address this problem.

SUMMARY OF THE INVENTION

Other features and advantages of the present invention will be set forth in the description of invention that follows, and in part will be apparent from the description or may be learned by practice of the invention. The invention will be realized and attained by the compositions and methods particularly pointed out in the written description and claims hereof.

*G. vaginalis* is frequently associated with BV. In addition to forming biofilms that are difficult to eradicate, this bacterium produces a cholesterol-dependent cytolysin (CDC), vaginolysin (VLY) VLY is one of the virulence factors of *G. vaginalis*. As with all CDC family members, VLY associates with cholesterol in the plasma membrane of host cells and forms large oligomeric pores. The activity of this enzyme is dependent upon the presence of cholesterol in the membrane.

Since HMG-CoA reductase inhibitors (statins) affect not only serum levels of cholesterol but also levels of cholesterol in membranes, we investigated whether or not statin use affected the vaginal microbiome. The results showed that the mean proportion of *G. vaginalis* amongst women taking statins was significantly lower relative to women not using statins. Women using statins had higher mean proportions of *Lactobacillus crispatus* relative to women with normal cholesterol levels, and higher levels of *Lactobacillus jensenii* relative to women with high cholesterol but not taking statins. In addition, in vitro, vaginal epithelial cells pretreated with the statin simvastatin were relatively resistant to vaginolysin and this effect was inhibited by cholesterol.

Thus, the compositions and methods disclosed herein prevent and/or treat bacterial vaginosis. The methods typically involve local, topical and/or systemic administration to vaginal epithelial cells of a composition comprising agents that decrease cholesterol levels in vaginal cells. In particular, the compositions comprise at least one statin and at least one agent that reduces cellular cholesterol uptake. Without being bound by theory, the invention uses statins or other cholesterol lowering drugs to produce a decrease in cholesterol in vaginal plasma membrane cells (e.g. epithelial cells) and thereby prevents or decreases the establishment of *G. vaginalis* as a predominant vaginal bacterial species. The effect is to prevent or lessen the VLY activity (such as the formation and maintenance of a bacterial biofilm, pore formation, cell lysis, etc.), and to permit or fostering the growth of competing species associated with vaginal health, such as *Lactobacilli*.

It is an object of the invention to provide methods of preventing or treating bacterial vaginosis (BV), or a disease or condition that is associated with BV, in a subject in need thereof, comprising administering to the subject a therapeutically effective amount of a composition comprising i) at least one statin and ii) at least one agent that inhibits cholesterol absorption. In some aspects, the statin is selected from the group consisting of lovastatin, atorvastatin, rosuvastatin, simvastatin, fluvastatin, pitavastatin, cerivastatin, and pravastatin. In some aspects, the agent that inhibits cholesterol absorption is a monobactam that does not have anti-bacterial activity or a plant phytosterol. In additional aspects, the monobactam is ezetimibe. In further aspects, the step of administering is performed intravaginally for either or both the at least one statin and the at least one agent that inhibits cholesterol absorption. In other aspects, the step of administering is performed systemically for at least one of: i) a statin, and ii) an agent that decreases cellular cholesterol absorption. In some aspects, the subject does not have high cholesterol. In further aspects, the disease or condition that is associated with BV is pre-term birth, peripartum infectious morbidity, a sexually transmitted disease, recurrent bacterial vaginosis and vaginal dysbiosis. In yet further aspects, the step of administering is performed by insertion of a vaginal ring comprising the at least one statin and the at least one agent that inhibits cholesterol absorption.

The invention also provides methods of promoting the growth of *Lactobacilli* in the vagina of a female human in need thereof, comprising administering to the female human an effective amount of a composition comprising i) at least one statin and ii) at least one agent that inhibits cholesterol absorption. In some aspects, the statin is selected from the group consisting of lovastatin, atorvastatin, rosuvastatin, simvastatin, fluvastatin, pitavastatin, cerivastatin, and pravastatin. In other aspects, the agent that inhibits cholesterol absorption is a monobactam that does not have anti-bacterial activity or a plant phytosterol. In additional aspects, the monobactam is ezetimibe. In additional aspects, the step of administering is performed intravaginally. In yet further aspects, the step of administering is performed by insertion of a vaginal ring comprising the at least one statin and the at least one agent that inhibits cholesterol absorption.

The invention further provides topical compositions comprising i) at least one statin, ii) at least one agent that inhibits cholesterol absorption, and iii) a pharmaceutically acceptable carrier, wherein the topical composition is suitable for administration to a human vagina. In some aspects, the statin is selected from the group consisting of lovastatin, atorvastatin, rosuvastatin, simvastatin, fluvastatin, pitavastatin, cerivastatin, and pravastatin. In other aspects, the agent that inhibits cellular cholesterol absorption is a monobactam that does not have anti-bacterial activity or a plant phytosterol. In further aspects, the monobactam is ezetimibe. In additional aspects, the topical composition is formulated for delivery via a vaginal ring.

DETAILED DESCRIPTION

The present invention provides compositions which, when delivered e.g. to vaginal epithelial cells by the methods disclosed herein, interfere with the action of VLY, and thus with the virulence and/or invasive ability of *G. vaginalis*. Without being bound by theory, it is believed that interference occurs as a result of decreasing the level of cholesterol in vaginal cells, thereby providing an environment that is better suited to the growth of beneficial microbes (e.g. *Lactobacilli*) in the vagina. Exemplary compositions comprise one or more HMG-CoA reductase inhibitors (statins) together with one or more agents that inhibit cholesterol absorption. In an exemplary aspect, the direct delivery of a combination of a statin and an agent that inhibits cholesterol absorption to vaginal epithelium reduces the growth of BV-associated bacteria and increases the growth of healthy bacteria such as lactobacilli. Advantageously, statins and cholesterol absorption inhibitors are already widely used for other purposes and are considered safe for long-term use.

As described in more detail elsewhere herein, in some aspects, the two types of agents are administered in a single composition; however, in other aspects, the two types of agents are administered separately in separate compositions. However, in the latter case, administration is generally, but not always, timed or arranged so that both of the agents are simultaneously present at the targeted site of activity (the vaginal wall and/or cells located therein). However, alternate administration (one agent and then another) is also encompassed.

In some aspects, compositions comprising these two types of agents are formulated for local, topical vaginal delivery. Local, topical intravaginal delivery avoids unwanted side effects that can accompany systemic delivery. In addition, higher concentrations of the active agents can be achieved where they are needed: on and in vaginal epithelial cells. However, systemic administration may also be employed, as may combination therapies comprising both topical and systemic administration. The methods disclosed herein involve delivery of the compositions to prevent and/or treat bacterial vaginosis and/or recurrent bacterial vaginosis, and/ or to prevent and/or reduce the incidence of associated complications such as acquisition of sexually transmitted diseases and pre-term births.

Statins

Statins function by inhibiting HMG-CoA reductase activity, thereby decreasing cholesterol synthesis and reducing serum levels of low density lipoproteins. Statins are typically administered orally to treat hyperlipidemia and reduce the risk of cardiovascular disease. In contrast, according to the present disclosure, one or more statins are preferably administered locally to vaginal tissue, in combination with one or more agents that reduces cholesterol absorption (described below).

Exemplary statins that may be used in the practice of the invention include but are not limited to: lovastatin, atorvastatin, rosuvastatin, simvastatin, fluvastatin, pitavastatin, cerivastatin, and pravastatin.

Agents that Reduce Cellular Uptake of Cholesterol

Agents that inhibit the absorption of cholesterol from the small intestine decrease the amount of cholesterol normally available to liver cells, leading them to absorb more from circulation, thereby lowering levels of circulating cholesterol.

One class of this type of agent is monobactams, usually monobactams that do not show antibiotic activity. One example is ezetimibe, a conformationally restricted analog based on the 2-azetidinone backbone. The exact mechanism of action of this exemplary cholesterol absorption inhibitor is not known, but it appears that ezetimibe blocks the critical mediator of cholesterol absorption, the Niemann-Pick C1-like 1 (NPC1L1) protein on the gastrointestinal tract epithelial cells as well as in hepatocytes; blocks aminopeptidase N, and interrupts a Caveolin 1-Annexin A2 complex involved in trafficking cholesterol. Another similar exemplary monobactam is Sch-48461 ((3R,4S)-1,4-Bis(4-methoxyphenyl)-3-(3-phenylpropyl)-2-azetidinone).

Plant-derived phytosterols are also cholesterol absorption inhibitors and may be used in the practice of the invention. These inhibitors appear to function by competing with cholesterol for absorption by several different mechanisms. Exemplary phytosterols that may be used in the practice of the present invention include but are not limited to: β-sitosterol, campesterol and stigmasterol, and preparations comprising one or more of these such as cytellin, a phytosterol preparation containing principally β-sitosterol.

Other examples of agents that inhibit (e.g. prevent, decrease or slow) cholesterol absorption include but are not limited to, for example, SCH 48461.

Exemplary Combinations of at Least One Statin and at Least One Agent that Prevents or Inhibits Cholesterol Uptake/Absorption Examples of combinations of statins and agents that decrease cholesterol absorption include but are not limited to, for example, ezetimibe and atorvastatin, and ezetimibe and simvastatin.

Compositions for Vaginal Delivery

Many formulations suitable for vaginal delivery of active agents are known, and many of these can be used to deliver the active agents of the compositions described herein. For example, the following United States patents and applications, the complete contents of each of which is herein incorporated by reference in entirety, describe suitable formulations which may be employed in full or on part, with or without the active agents or drugs disclosed therein: U.S. Pat. Nos. 4,551,148 and 5,266,329 describe emulsions and suspensions for vaginal delivery with characteristics of bioadherence to the vaginal surface; U.S. Pat. No. 5,514,698 describes long-lasting vaginal creams that have a stable viscosity in the human body; US patent application 20030215471 discloses suitable surfactant free topical compositions; US patent application 20060165803 describes additional mucoadhesive compositions suitable for vaginal delivery of active agents; US patent application 20080008740 describes carriers comprising a hydrophilic gel-forming base; US patent application 20060240111 discloses semisolid mucoadhesive formulations for vaginal application; and US patent application 20170014458 describes vaginal tablets which include an excipient suitable for conferring upon the tablet the properties of vaginal wall mucoadhesion and sustained release.

The compositions are generally formulated with the active ingredients, together with one or more pharmaceutically acceptable carriers, diluents and/or excipients sufficient to achieve a suitable concentration of active agent. In some aspects, both of the active agents are present in a single composition. However, the use of two different preparations each of which contains only one of the two agents may also be used. In general, the concentration of a statin in a composition for vaginal delivery is in the range of from about 0.001 mg/L to about 10 mg/L, and is more usually in the range of from about 0.1 mg/L to about 0.5 mg/L. The concentration of a cholesterol uptake inhibitor in a composition for vaginal delivery is generally in the range of from about 0.001 mg/L to about 1 mg/L, and is more usually in the range of from about 0.005 to about 0.05 mg/L. For inhibitors that are physterols, the concentrations are generally e.g. at least about 10 fold or more higher, e.g. from at least about 0.5 to 5 mg/L, or about 1 mg/L to 10 mg/L. In addition, those of skill in the art will recognize that the concentration of active agent in a composition will vary depending e.g. on the mode of delivery. For example, when delivered by a vaginal ring, the goal is to achieve an effective sustained local concentration.

The compositions are frequently formulations including, but not limited to, aqueous or oily suspensions, solutions, emulsions (e.g. creams), semisoft ointments, pastes, lotions, gels, jellies, hydrogels, sprays, foams, solids and the like. The compositions may also be formulated as a dry product for reconstitution with a suitable vehicle before use. Such preparations may contain one or more additives including, but not limited to: suspending agents, dispersing or wetting agents, emulsifying agents, aqueous and non-aqueous vehicles, preservatives, lipophilic excipients, hydrating agents, pH regulating agents, bioadhesion and/or mucoadhesion promoting agents, stabilizers, antimicrobial agents, buffers, coloring agents, adjuvants, etc. The active agents may be comprised in micro- or nanoparticles that are suspended in a carrier, and the formulations may or may not be sustained, slow-release formulations.

Suspending agents include, but are not limited to, sorbitol syrup, methyl cellulose, glucose/sugar syrup, gelatin, hydroxyethyl cellulose, carboxymethyl cellulose, aluminum stearate gel, and hydrogenated edible fats. Emulsifying agents include, but are not limited to, lecithin, sorbitan monooleate, and acacia. Preservatives include, but are not limited to, methyl or propyl p-hydroxybenzoate, dehydroacetic acid, benzyl alcohol, and sorbic acid. Dispersing or wetting agents include, but are not limited to, poly (ethylene glycol), glycerol, bovine serum albumin, Tween®, Span®, sodium cocoyl glutamate, disodium cocoyl glutamate, *Quillaja saponaria* wood extract, caprylyl/capryl glucoside, etc. Lipophilic excipients include glyceryl stearates and derivatives, for example, polyethylene glycol stearates, ketostearyl alcohols, polyoxyethylene glycol ethers of n-alcohols (lauryl, cetyl, stearyl and myristyl alcohol), liquid paraffin, lecithin oil, glycerol and the like. Hydrating agents such as Seabuckthorn juice and Aloe barbadensis leaf juice. pH regulating agents include, for example, lactic acid, sodium tartrate, disodium succinate, trisodium citrate, and the like.

At least one agent that promotes bioadhesion, e.g. mucoadhesion is generally included in the compositions, examples of which include but are not limited to: cellulose polymers, cellulose derivatives such as hydroxypropylmethyl cellulose, hydroxyethyl cellulose, hydroxypropyl cellulose, sodium carboxymethyl cellulose, methyl cellulose, ethyl cellulose, ethyl hydroxyethyl cellulose, carboxymethyl cellulose and modified cellulose gum; crosscaramellose; modified starch; acrylic polymers comprising carbomer and its derivatives; and agents such as polyethylene oxide; chitosan; gelatin; sodium alginate; pectin; scleroglucan; xanthan gum; guar gum; poly-co-(methyl vinyl ether-maleic anhydride); colloidal anhydrous silica or polyacrylic acid derivative polymers, such as carbomers, polycarbophils and the like, and mixtures thereof. In a particular aspect, the one or more mucoadhesive excipients possess gel-forming properties.

Some examples of materials which can serve as pharmaceutically acceptable carriers include, but are not limited to: ion exchangers, alumina, aluminum stearate, lecithin, serum proteins (such as human serum albumin), buffer substances (such as Tween 80®, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutically acceptable salts may also be included, i.e. relatively non-toxic, inorganic and organic acid addition salts, and base addition salts, Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-β-hydroxynaphthoates, gentisates, isethionates, di-p-toluoyltartrates, methanesulfonates, ethanesulfonates, benzenesulfonates, p-toluenesulfonates, cyclohexylsulfamates and laurylsulfonate salts, and the like. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use. ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

Further materials as well as formulation processing techniques and the like are set out in Part 5 of Part 5 of Remington's "The Science and Practice of Pharmacy", 22.sup.nd Edition, 2012, University of the Sciences in Philadelphia, Lippincott Williams & Wilkins the content of which is incorporated herein by reference.

Vaginal compositions disclosed herein may be delivered in any of many different forms or by any of many different mechanisms, including but not limited to: as a cream, lotion, semi-solid or gel that is administered e.g. via a "plunger" or other style applicator; via pessaries or ovules; as a suppository, tablet or hard or soft gelatin capsule that dissolves in the vagina; in a vaginal capsule, film or sponge; via a "tampon" that is impregnated with a composition; via a "pouch" or other permeable device that is placed in the vagina and from which the composition leaches onto the vaginal walls; of via a liquid douching preparation; via a vaginal ring (single or multi-segmented), akin to the NuvaRing® and dapavirine rings; etc. The compositions may also be used as or comprised within lubricants (e.g. for sexual intercourse), or as or comprised in lubricants/coatings on condoms, etc. A device or means for delivery may or may not be biodegradable. Typically, the compositions are creams, lotions, semi-solids or gels that are administered e.g. via a "plunger" style applicator, which may be refillable and/or disposable. More preferably the compositions are delivered via an insertable ring that slowly releases the active agents and that is changed e.g. about monthly. Examples of vaginal rings that may be employed are found, for example, in U.S. Pat. Nos. 4,822,616 and 6,126,958 and in US patent applications 20030060785 and 20030152625, the complete contents of each of which is hereby incorporated by reference.

Compositions for Systemic Delivery

Systemic delivery of statins and/or cholesterol absorption inhibitors are known and typically include one or both of the active agents and a pharmaceutically acceptable carrier. Generally, such compositions are delivered orally in the form of tablets or pills, but other delivery forms are also encompassed, e.g. capsules, liquids, etc. While not usual, in some circumstances, delivery may be by injection The compositions and concentrations of active agent present in such compositions are generally the same as those used to lower cholesterol, e.g. ranging from about 1 to about 80 or 100 mg per dose, depending on the agent that is used. Those of skill in the art are aware of established guidelines for dosing statin and cholesterol absorption inhibitors.

For systemic delivery, the compositions generally comprise one or both of the active agents i.e. two different compositions, one comprising one of the active agents, may be also be used. However, it is more usual to include both agents in a single preparation.

Oral dosage forms generally include the components listed above for vaginal delivery, but formulated as a solid using techniques that are known (e.g. see Remington's supra).

Co-Delivery of Other Active Agents

In some aspects, the compositions described herein, especially compositions that are delivered vaginally, may also include useful agents such as steroids (e.g. for birth control such as estrogen and/or a progestogen, or for hormone replacement therapy, etc.), antibiotics, etc.

Methods

Described herein are methods for treating and/or preventing one or more symptoms of disease and conditions that are caused and/or exacerbated by the presence of cholesterol or high levels of cholesterol in vaginal cells, e.g. the cells of the vaginal wall. Examples of such disease/conditions include but are not limited to: BV, vaginal dysbiosis (unfavorable balance of microbial species such as low or no *Lactobacilli* and/or high *Gardnerella* species, high proportions of anaerobic and strictly anaerobic bacteria, etc.), pre-term birth, peripartum infectious morbidity, the acquisition of sexually transmitted disease, etc. Those of skill in the art will recognize that "treating" an individual for a disease or unwanted condition may involve complete eradication of all symptoms (i.e. "curing" the disease). Alternatively, much advantage can accrue even if a complete cure is not achieved, e.g. if one or more symptoms of the disease/condition are lessened or decreased in severity or time of duration. For example, the frequency or length of duration of one or more symptoms may be decreased. As a further example, the microbiome of a treated subject may not completely change to a *Lactobacillus*-dominated profile, but may be changed to have at least an increased population of one or more *Lactobacilli* and/or a decreased the population of undesirable bacteria such as *G. vaginalis*. Similarly, pre-term birth may not be entirely prevented but the gestation period may be lengthened (e.g. by a few weeks) to within a period of time that is safer for the mother and infant.

The methods disclosed herein may include a step of identifying or diagnosing suitable candidates for the treatments. The subjects who are treated using the methods described herein generally have one or more symptoms of BV, including but not limited to: a change in color, odor or amount of discharge from the vagina; vaginal itching or irritation; pain during intercourse; painful urination; light vaginal bleeding or spotting, etc. Typically, a suspected infection is diagnosed (verified) by swabbing the vagina and detecting the types and amounts of bacteria present, with changes in the numbers of healthy bacteria (e.g. *Lactobacilli*) and a general increase in the number of bacteria being characteristic. An increase in the pH of the vagina is also generally present. Diagnoses may be established and/or confirmed, using, for example, known techniques such as the Amsel criteria, the Nugent score, the Hay/Ison criteria, Gram stains, presence of "clue cells" in a wet mount, etc.

On the other hand, in some aspects, prevention rather than treatment is the goal. In such cases, the subject may have no symptoms or positive indicators of BV, but may still benefit greatly by administration of the compositions described herein. For example, a woman may or may not have low *lactobacillus* colonization or colonization by *G. vaginalis*, but may still benefit from therapy. Examples of risk factors which can make women candidates for treatment include but are not limited to: a CST IV type microflora profile; African American origin; being of childbearing age or being pregnant; being at risk for acquiring a sexually transmitted disease (e.g. those with new and/or multiple sex partners, sex workers, etc.); having unprotected sexual intercourse; frequent or long term use of high doses of the spermicide nonoxynol-9; having a history of BV; douching; use of antibiotics; use of an intrauterine device; being peri- or post-menopausal; at risk for peripartum infectious morbidity; etc.

In the practice of the present methods, a goal is to lower cholesterol levels in cells of the vaginal plasma membrane. While the role of cholesterol in cholesterol dependent cytolysin function is not fully understood, studies have shown that high levels of cholesterol (50 mol %) are required for pore formation in lipid micelles and that cholesterol dependent cytolysins fail to form pores at 40 mol % cholesterol. Thus, in some aspects, a goal of the present methods is to lower the overall concentration of cholesterol in plasma membranes of cells and/or to lower the concentration of cholesterol within lipid rafts in membranes and/or to reduce the abundance of lipid rafts in plasma membranes of the vaginal wall. The reduction is generally at least about 5, 10, 15, 20, 25, 30, 35, 40, 45, or 50% or more, compared to normal levels.

Generally, a healthy level of cholesterol (HDL and LDL combined) in blood is considered to be less than 200 mg/dL and/or with a level of HDL that exceeds about 40 mg/dL. For systemic administration, mean optimal concentrations of statins in human serum at therapeutic doses range from about 1 to about 15 nmol/liter, and these levels may be sufficient in the practice of the present invention.

In some aspects, the patient that is treated may already be taking one or both of a statin and an agent that inhibits cholesterol absorption in order to lower their cholesterol. Such administration is typically oral and thus systemic. For such subjects, it may be preferable to increase the oral dose about that which would be used to lower cholesterol, or to add intravaginal delivery. In other aspects, the subject that is treated is not already taking cholesterol lowering medications and administration may be vaginal, systemic or both. Thus, the subject may or may not have high cholesterol and may or may not be undergoing treatment for high cholesterol.

In some aspects, administration is intravaginal and is typically once or twice daily. However, administration may be more or less frequent, depending on the circumstances. For example, during an acute (active) infection, administration may be twice or more daily for a period of 3-10 days, whereas in the absence of an acute infection (e.g. to maintain vaginal health and prevent recurrence after an infection is cured, or before an infection is acquired), administration may be less frequent, e.g. once daily, once per week, bi-weekly, monthly, etc. If a sustained release formulation is utilized, the frequency of administration is adjusted accordingly. In some aspects, once a target microbial population is reached, administration may be stopped or decreased to a lower frequency.

In other aspects, administration is systemic, e.g. oral, and is generally once daily, although for an acute infection, more frequent administration (e.g. 2-4 times a day) is possible. However, as for vaginal administration, for maintenance of a healthy vaginal microbiome on an ongoing basis, administration may be less frequent, e.g. once per week, bi-weekly, once per month, etc.

In some aspects, administration involves a combination of intravaginal plus systemic administration. For example, one or both agents may be administered by both routes, e.g. both may be administered by both routes; or one or the other of the statin and the cholesterol uptake inhibitor may be administered intravaginally while the other is administered systemically; or one of the statin and the cholesterol uptake inhibitor may be administered intravaginally or systemically and a combination of the two may be administered by another route.

In further aspects, one or more of the compositions described herein are administered in conjunction with (together with) one or more other therapies for the prevention or treatment of BV, recurrent BV, sexually transmitted diseases, pre-term birth, etc. Exemplary agents/treatments including but not limited to: various antimicrobial agents such as antibiotics (e.g. nitroimidazoles such as metronidazole and tinidazole; clindamycin, etc.); anti-retroviral agents; compounds such as fibrates (e.g. Fenofibrate, gemfibrozil, etc.) and cyclosporine which increases blood levels of ezetimibe; etc. In some aspects, the present methods are used following administration of an antibiotic to promote the repopulation of the vagina with healthy microbes.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLES

Example 1. Association Between Statin Use, the Vaginal Microbiome, and *Gardnerella vaginalis* Vaginolysin-Mediated Cytotoxicity

*Gardnerella vaginalis* is significantly more abundant in the vaginal microbiome of AA women. *G. vaginalis* is a common member of CST IV and has a very strong association with BV. It is present in nearly all cases of BY, and it forms biofilms on the vaginal epithelium that contribute to the poor cure rates of antimicrobial therapy.

Cholesterol trafficking in the human body is complex. It is synthesized by cells but can also come from dietary sources. It is in constant flux between intracellular compartments, the plasma membrane and extracellular compartments. Low density lipoproteins (LDL) are used to shuttle cholesterol through the blood to cells and tissues in the body when it is required and high density lipoproteins are used to rid the body of cholesterol when it is in excess. High LDL levels are associated with cardiovascular disease. Hence, when high LDL levels are detected in serum, efforts are made to reduce them.

Statins are pharmacologic agents that inhibit HMG-CoA reductase, an enzyme that plays a key role in cholesterol synthesis. Consequently, statins reduce cholesterol synthesis and lower serum cholesterol, which reduces the risk for cardiovascular disease. While statins are designed to reduce extracellular cholesterol in blood in the form of low density lipoprotein, they can also reduce cholesterol in the plasma membranes of cells and erythrocyte membrane cholesterol levels are reported to decrease following initiation of statin therapy. Some studies indicate an association between statin use and reduced severity of certain infections, including pneumonia, although there is also conflicting data. A recent study found that, in vitro, simvastatin treatment of human airway epithelial cells reduced the pore-forming activity of pneumolysin, a CDC produced by *Streptococcus pneumoniae*.

This example reports investigations of the relationship between statin use and the vaginal microbiome, and the effect of simvastatin on VLY activity.

Materials and Methods

Participant Recruitment

Subjects for this study were selected from the 4,306 women enrolled in the Vaginal Human Microbiome Project at VCU (VaHMP). Participants recruited from outpatient clinics at the Virginia Commonwealth University Medical Center and the Virginia Department of Health following written, informed consent from 2009-2013. The Institutional Review Boards for Human Subjects Research at VCU (Panel B) and the Virginia Department of Health reviewed and approved this study. Participants filled out a detailed questionnaire that included questions about ethnicity, education, employment, health habits, dietary habits, and sexual history. Clinicians also filled out a diagnosis form at the time of each visit that included information about the purpose of each visit, and any diagnoses. Inclusion criteria for VaHMP included women age at least 18 years of age who were able to provide informed consent and who were willing or already scheduled to undergo a vaginal examination using a speculum. The inclusion criterion for the subset of women included in this study was current statin use. Control groups included women who reported normal cholesterol levels and no statin use and women who reported high cholesterol levels and no statin use selected randomly from the VaHMP database. The control groups were matched for age and ethnicity to have the same proportionality for every 5 years amongst AA and EA groups. Statin use and non-use and cholesterol levels were initially ascertained by self-report and confirmed through medical record abstraction.

Sampling and Sample Processing

Clinicians used CultureSwab EZ polyurethane foam swabs (BD) to obtain specimens from the mid-vaginal wall during a speculum examination. DNA was extracted from the swabs within 4 h of collection using a PowerSoil® kit (MoBio). Surveys of the 16S rRNA genes present in the samples were generated as part of the Vaginal Human Microbiome Project (Fettweis, et al. The Vaginal Microbiome: Disease, Genetics and the Environment. Nat Preced [Internet]. 2011 Mar. 4 [cited 2016 Jul. 13]:(713); available from the website located at precedings.nature.com/documents/5150/version/2). Sequences were classified using a local installation of RDP Classifier (Huse et al. PLoS Genet. 2008 Nov.; 4(11):e1000255) (0.8 cut-oft) and the STIRRUPS analysis platform (Fettweis et al. BMC Genomics. 2012:13 Suppl 8:S17).

16S rRNA Gene Survey

The V1-V3 hypervariable regions of the bacterial 16S rRNA gene were amplified by PCR using barcoded primers. The 16S primers contain the A or B Titanium sequencing adapter (shown in italics), followed immediately by a unique variable (6-9 base) barcode sequence and finally the 5' end of primer. The forward primer was a mixture (4:1) of the primers Fwd-P1 (5'-CCATCTCATCCCTGCGTGTCTC-CGACTCAG BBBBBB AGAGTTYGATYMTGGCTYAG; SEQ ID NO: 1) and Fwd-P2 (5'-CCATCTCATCCCTGCGT-GTCTCCGACTCAGBBBBBBAGARTTTGATCYTGGT-TCAG; SEQ ID NO: 2), where "B" stands for C, G or T. The reverse primer was Rev1B (5'-CCTATCCCCTGTGTGCCT-TGGCAGTCTCAG ATTACCGCGGCTGCTGG; SEQ ID NO: 3). PCR products were sequenced using the Roche 454 GS FLX Titanium platform. These data were generated as part of the Vaginal Human Microbiome Project. Raw sequence data from the project is available from the Short Read Archive at NCBI (projectID phs000256). A deep sequencing approach was used with a median 24,030 reads/sample. Samples with fewer than 5,000 reads were excluded from the analysis.

Reads that met the following criteria were processed: 1) valid primer and multiplex identifier sequences were observed; 2) less than 10% of base calls had a quality score less than 10; 3) the average quality score was greater than Q20; and 4) the read length was between 200 and 540 bases. Sequences were classified using a local installation of the RDP classifier (0.8 cutoff) and using STIRRUPS, an analysis platform that employs the USEARCH algorithm combined with a curated vaginal 16S rRNA gene database.

Statistics

Sequencing read counts were converted to proportions for all samples to determine the percent of the total microbiome that each bacterial species contributed. The predominant taxon in a sample refers to the taxon for which the largest number of reads were assigned taxonomic classification with confidence (i.e. the highest percentage of reads in the sample). Microbiomes were categorized by community state types (CST) similar to a previous study (Ravel et al. Proc Natl Acad Sci USA. 2011 Mar. 15; 108 Suppl 1:4680-7.). CST I, microbiomes in which the proportion *L. crispatus*>=30% and predominant taxon=*L. crispatus*; CST II, proportion *L. gasseri*>=30% and predominant taxon=*L. gasseri*; CST III, proportion *L. iners*>=30% and predominant taxon=*L. iners*; CST IV, no proportions of any one species of *Lactobacillus*>=30%; CST V, proportion *L. jensenii*>=30% and predominant taxon=*L. jensenii*.

Linear discriminant analysis effect size (LEfSe) applies a Kruskal-Wallis rank sum test for each bacterium, then uses linear discriminant analysis to estimate effect size (38). The effect size is the contribution of a variable to the ability to distinguish two different groups. The barplot indicating the effect size of bacterial species that correlate with statin use was generated through LEfSe using a minimum cut-off LDA score of three and reducing permutations to 100,000 to avoid very low abundance organisms.

The boxplot of *G. vaginalis* has whiskers that extend to the highest/lowest value within 1.5 times the interquartile range. Data beyond the end of the whiskers are outliers and are plotted as points. A Wilcoxon rank sum test with continuity correction was used to test whether the median and mean proportions of *G. vaginalis*, *L. crispatus*, and *L. jensenii* followed the same distribution for groups of subjects (Statin/no statin use high cholesterol/no statin use low cholesterol, African/European ancestry). Analysis was conducted and plots were created using the R language for statistical computing and plotting package ggplot2.

Media and Culture Conditions

*G. vaginalis* strain AMD was grown in brain heart infusion supplemented with 10% human serum anaerobically at 37° C. *E. Coli* was grown at 37° C. under atmospheric conditions. The human vaginal epithelial cell line VK2/E6E7(Fichorova et al. Biol Reprod. 1997 October: 57(4): 847-55). (ATCC®-CRL-2616™) was cultured at 37° C. and 5% $CO_2$ in Keratinocyte-Serum Free medium with 0.1 ng/ml human recombinant EGF, 0.05 mg/ml bovine pituitary extract, and additional calcium chloride 44.1 mg/L (final concentration 0.4 mM).

Expression and Purification of Recombinant VLY

DNA was extracted from *G. vaginalis* strain AMD using the DNeasy® Blood and Tissue kit (Qiagen). The v/v gene was amplified using primers VaginolysinFWD (5'-GGAAGGGATCCGATTCTTCTGCAAAGCCTTCTGC-3'; SEQ ID NO: 4) and VaginolysinREV (5'-GGAAGCTC-GAGTCAGTCATTCTTTACAGTTTCAGCAAC-3'; SEQ ID NO: 5) as previously described (Gelber et al. J Bacteriol. 2008 June; 190(11):3896-903). Purified PCR product was restricted with BamHI and XhoI and ligated to pET32. Plasmid from a colony that grew on LB agar containing 100 μg ampicillin/mL was confirmed by DNA sequencing and transformed into *E. coli* strain BL21(DE3) CodonPlus pRIPL (Agilent technologies). Cultures were grown in 1 L LB containing 100 μg amp/mL and 35 μg chloramphenicol/mL to exponential phase, induced with 1 mM IPTG for 2 hours, and the bacteria were collected by centrifugation. Bacteria were lysed in a French pressure cell in B-PER™ (ThermoFisher Scientific) containing protease inhibitors (EDTA-free cOmplete™, Sigma) and the lysate was cleared by centrifugation and filtration. The protein was purified by cobalt affinity chromatography (His-Pur™, Thermo-Fisher Scientific) according to manufacturer instructions, eluted in 0.25 M imidazole, and dialyzed against 1× phosphate buffered saline (PBS). The affinity tag was removed by thrombin digestion (Sigma-Aldrich. Thrombin CleanCleave™ Kit).

Cytotoxicity Assay

VK2/E6E7 cell monolayers were established in 96-well plates in 100 μL Keratinocyte media (Life Technologies Keratinocyte-SFM) per well. Once the monolayers reached 70% confluence, a fresh stock solution of 1 mg simvastatin/ml ethanol was prepared and monolayers were pre-treated with a final concentration of 1 μg simvastatin/ml or an equal volume (1 μl/ml) of ethanol for 48 hours in the presence or absence of 5 μg cholesterol/ml (Sigma, cholesterol balanced with methyl-β-cyclodextrin). Following the 48 hr pretreatment, media was replaced with fresh media containing ethanol or simvastatin but no serum or any other source of cholesterol, and purified recombinant VLY was added at a starting concentration of 20 μg/ml and 1:2 dilutions were made. The monolayers were incubated for 60 min at 37° C., trypan blue staining was performed, and pictures were immediately taken using a digital camera mounted on a light microscope. Media from unstained replicate wells was analyzed using the Cytotoxicity Detection Kit for quantification of extracellular lactate dehydrogenase (Roche). The experiments were performed 3 times and each experimental replicate contained technical triplicate samples. Results for individual LDH assays were compared using one-way analysis of variance (ANOVA) with Tukey post-test for comparison of individual groups.

Results

Statin Use is Associated with Vaginal Community State Type

The 16S rRNA survey profiles of vaginal swabs from 72 AA and 61 EA women who were using statins at the time of sampling were analyzed, 83 AA and 69 EA women who reported high cholesterol but were not taking statins, and 160 AA and 156 EA women who did not report high cholesterol and were not taking statins. Information about the subject groups is listed in Table 1. Tukey multiple comparison indicated that within the ethnic groups, there were no significant differences in any of the variables considered, including mean age, pregnancy status, douching, number of sexual partners, smoking, hormone replacement therapy, alcohol consumption, income, or other variables listed in Table 1, between statin users, women with high cholesterol but no statin use, and women who reported that they did not have high cholesterol. Data analysis showed that the statin-using group appeared to have a higher overall proportion of the healthy *Lactobacillius* species *L. crispatus* and high diversity profiles were less common in this group relative to those who were not taking statins, regardless of cholesterol level (not shown). We used a system of categorizing community state types (CST) that was similar to what has been published previously (Ravel et al. Proc Natl Acad Sci USA. 2011 Mar. 15; 108 Suppl 1:4680-7) and found that CST I was significantly more common in AA statin users relative to non-statin users, regardless of whether they reported normal (Fisher test p=0.0042) or high cholesterol (p=0.0297) (Table 2). Furthermore, CST IV was significantly less common in AA statin users versus non-statin users relative to non-statin users with both normal (p=0.0068) and high cholesterol levels (p=0.0099). There was a similar trend in EA statin users but the increase in CST I and the decrease in CST IV were not significant in this group.

TABLE 1

Information about study participants

|  | AA statin yes | AA high cholesterol/ no statin | AA normal cholesterol/ no statin | EA statin yes | EA high cholesterol/ no statin | EA normal cholesterol/ no statin |
|---|---|---|---|---|---|---|
| Participants n | 72 | 83 | 160 | 61 | 69 | 156 |
| Age (mean) | 51.6 | 51.9 | 50.9 | 51.1 | 50.9 | 50.3 |
| Post-menopausal | 44(61%) | 49(59%) | 91(57%) | 34(56%) | 34(49%) | 73(47%) |
| Menstrual cycle phase (days last period) |  |  |  |  |  |  |
| Menstruation (day 1-5) | 2(3%) | 3(4%) | 5(3%) | 3(5%) | 3(4%) | 4(3%) |
| Follicular phase (day 6-14) | 4(6%) | 3(4%) | 7(4%) | 3(5%) | 5(7%) | 9(6%) |
| Luteal phase (day 15-28) | 6(8%) | 6(7%) | 10(6%) | 5(8%) | 5(7%) | 13(8%) |
| >28 days | 4(6%) | 5(6%) | 11(7%) | 4(7%) | 7(10%) | 9(6%) |
| NA | 57(79%) | 66(80%) | 127(80%) | 46(75%) | 49(71%) | 121(77%) |
| Taking hormonal replacement therapy | 4(6%) | 3(4%) | 14(9%) | 5(8%) | 5(7%) | 16(10%) |

TABLE 1-continued

Information about study participants

|  | AA statin yes | AA high cholesterol/ no statin | AA normal cholesterol/ no statin | EA statin yes | EA high cholesterol/ no statin | EA normal cholesterol/ no statin |
|---|---|---|---|---|---|---|
| Pregnant | 2 (3%) | 2 (2%) | 1 (1%) | 1 (2%) | 1 (1%) | 4 (3%) |
| Douche in last month | 7(14%) | 11 (19%) | 24 (15%) | 6 (10%) | 4 (6%) | 3 (2%) |
| Sex partners past year | | | | | | |
| 0 | 15 (21%) | 19 (24%) | 31 (19%) | 13 (21%) | 14 (20 %) | 26 (17%) |
| 1 | 34 (47%) | 42(53%) | 80 (50%) | 34 (59%) | 34 (49%) | 89 (57%) |
| >1 | 11 (15%) | 7 (9%) | 23 (14%) | 7 (11 %) | 7 (10%) | 8(5%) |
| N/A | 12(17%) | 15(18%) | 26(16%) | 7(11%) | 14(20%) | 33(21%) |
| Current smoker | 27 (38%) | 32 (40%) | 66 (41%) | 16 (27%) | 24 (35%) | 13 (36%) |
| Yogurt consumption >1 per week | 26 (36 %) | 39 (49%) | 65 (41%) | 33 (55%) | 37 (54%) | 92 (72%) |
| Alcohol >0 past week | 24 (33%) | 20 (25 %) | 48 (30%) | 22 (37%) | 22 (32%) | 67 (49%) |
| Income | | | | | | |
| <15K | 32 (44%) | 40 (48%) | 57 (36%) | 14 (23%) | 15 (22%) | 14 (10%) |
| 15K-20K | 7 (10%) | 11 (13%) | 21 (13%) | 2 (3%) | 6 (9%) | 3 ( 2%) |
| 20K-40K | 14 (19%) | 13 (16%) | 41 (26%) | 5 (8%) | 7 (10%) | 17 (12%) |
| 40K-60K | 4 (6%) | 7 (8%) | 5 (3%) | 8 (13%) | 7 (10%) | 26 (19%) |
| 60K-80K | 2 (3%) | 2 (2%) | 6 (4%) | 12 (20%) | 12 (17%) | 17 (12%) |
| >80K | 4 (6%) | 3 (4%) | 10 (6%) | 17 (28%) | 20 (29%1) | 59 (43%) |

All parameters listed in the table were self-reported. Statin use or non-use was confirmed by medical record abstraction.

TABLE 2

Statin use affects community state type

| Community state type | AA statins | AA high cholesterol | AA normal cholesterol | EA statins | EA high cholesterol | EA normal cholesterol |
|---|---|---|---|---|---|---|
| CST I | 28% (20) | 13% (11) | 12% (19) | 26% (16) | 19% (13) | 19% (26) |
| CST II | 3% (2) | 5% (4) | 1% (1) | 10% (6) | 7% (5) | 8% (11) |
| CST III | 29% (21) | 23% (19) | 29% (46) | 21% (13) | 22% (15) | 23% (31) |
| CST IV | 37% (27) | 59% (49) | 58% (92) | 38% (23) | 51% (35) | 46% (83) |
| CST V | 3% (2) | 0 | 1% (2) | 5% (3) | 1% (1) | 4% (5) |

Statin Use is Associated with Decreased Abundance of *G. vaginalis*

Figure 1A:
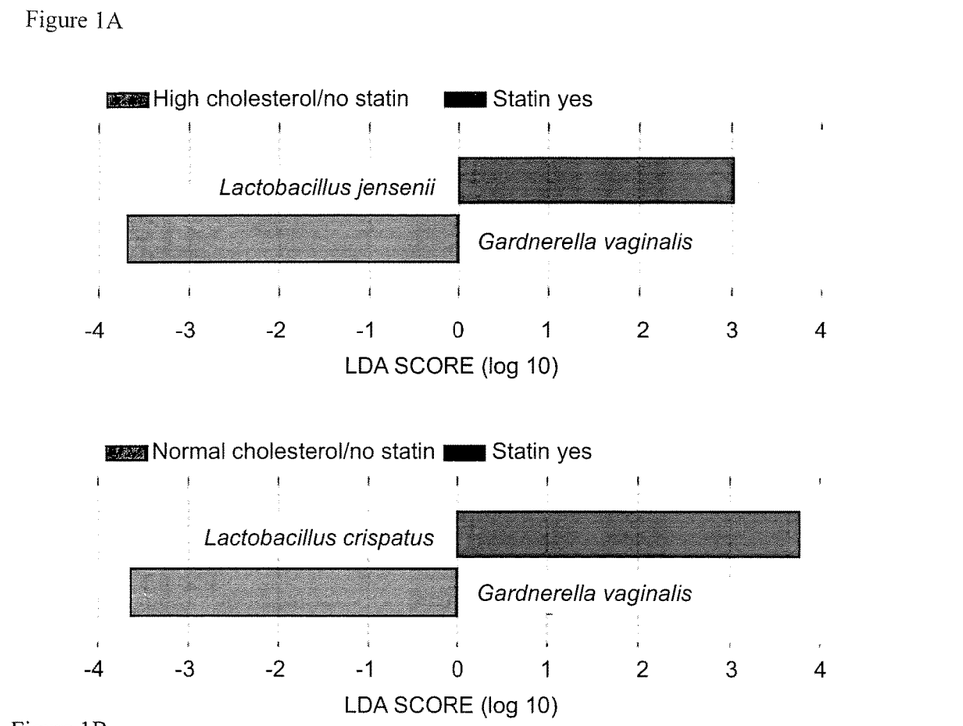
FIGS. 1A and B. The proportion of *G. vaginalis* is lower in statin users. A) Taxa that occurred in significantly different proportions in the vaginal microbiomes of statin users were detected by LEfSE analysis. Taxa significantly higher in women taking statins are on the right (positive x-axis) and taxa significantly lower (*G. vaginalis*) is in on the left (negative x-axis). The chart on top compares vaginal microbiota from women with high cholesterol who were not taking statins to women taking statins and the lower chart compares vaginal microbiota from women with normal cholesterol who were not taking statins to women taking statins B) Boxplot of *G.vaginalis* proportions in subjects grouped based on ethnicity and subgrouped based on statin use and normal versus high cholesterol, with whiskers that extend to the highest/lowest value within 1.5 times the interquartile range, outliers beyond the whiskers are plotted as points. The horizontal line in each box indicates the median. A Wilcoxon rank sum test with continuity correction was used to test whether the proportion of BV-associated bacteria followed the same distribution for groups of subjects (statin/high cholesterol no statin/no high cholesterol, African/European ancestry).
Figure 1B:
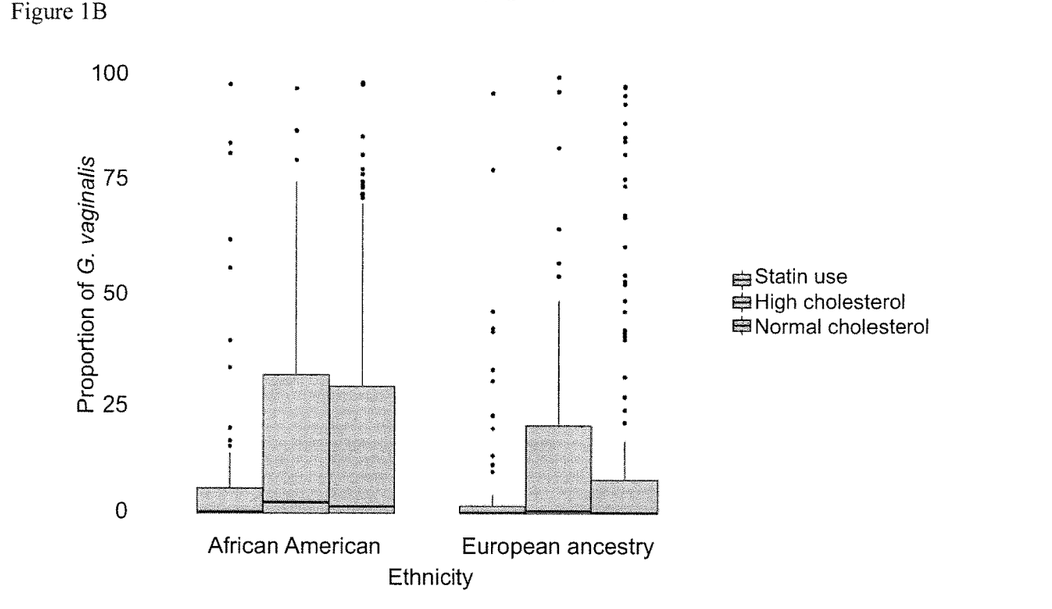

Linear discriminant analysis (LDA) effect size (LEfSe) was used to determine whether specific bacterial taxa were significantly associated with statin use. FIG. 1A illustrates that, according to LEfSe, the proportion of *G. vaginalis* was significantly lower in statin users (8.3%) relative to non-statin users with either normal (15.6%; Wilcoxon p=0.026) or high cholesterol (16.7%; p=0.047). In contrast, the proportion of *L. jensenii* was greater in statin users (3.9%) relative to those who reported high cholesterol but were not taking statins (2.9%; p=0.011) whereas the proportion of *L. crispatus* was higher in statin users (23.9%) relative to those who did not report high cholesterol (14.7%; p=0.013) and were not taking statins. The mean proportion of *L. crispatus* in those who reported high cholesterol but were not taking statins was 17.3%, which followed a similar trend but did not reach statistical significance (p=0.068). FIG. 1B shows the relationship between the proportion of *G. vaginalis* and statin use and ethnicity. FIG. 1B also reveals a negative association between statin use and colonization by *G. vaginalis* relative to AA women with normal cholesterol levels who were not using statins (p=0.0083) and AA women with high cholesterol who were not using statins (p=0.0439).

Simvastatin Treatment Protects Vaginal Epithelial Cells from VLY

Figure 2A:
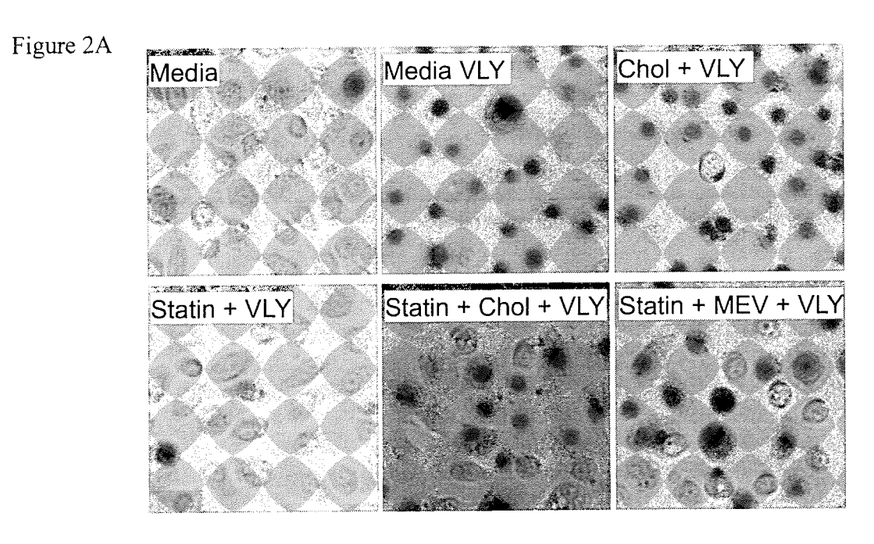
FIGS. 2A and B. Statins reduce vaginolysin-mediated cytotoxicity. A) VK2/E6E7 vaginal keratinocytes were incubated in control media or media containing 5 µg cholesterol/ml (Chol), 1 µg simvastatin ml (Statin), simvastatin and cholesterol, or simvastatin and 1 mM mevalonate for 48 hours. The cells were then left unchallenged or challenged with 10 VLY/mL for 1 hour. Trypan blue staining was performed to monitor rounding and permeabilization (observed as central darkening of the cells). B) VK2/E6E7 cells pre-treated with control, simvastatin, cholesterol, simvastatin and cholesterol, or simvastatin and mevalonate, and then challenged with 10 or 5 µg VLY/mL. Lactate dehydrogenase release assay was used to quantify permeabilization of the cells. * p<0.05, ** p<0.005 using one-way ANOVA with Tukey post-test for comparison of individual groups.
Figure 2B:
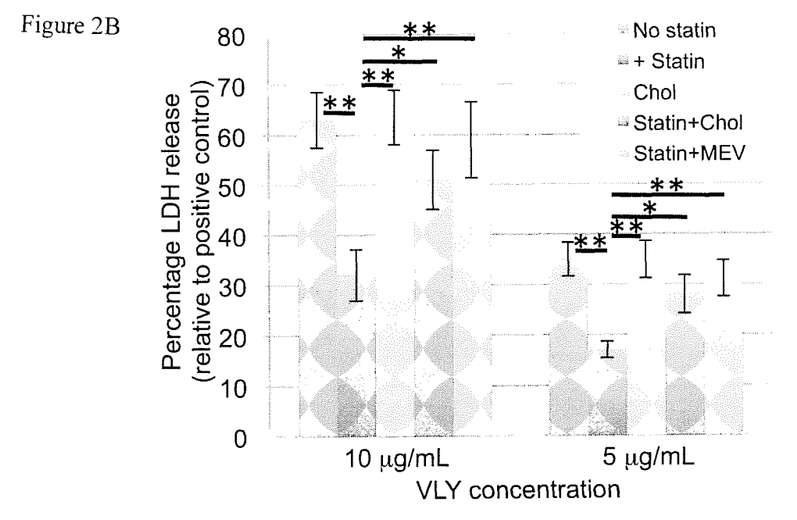

The decrease in the proportion of *G. vaginalis* observed in the statin treatment group could be due, in part, to an effect of host plasma membrane cholesterol depletion on the function of the cholesterol-dependent cytolysin vaginolysin (VLY). To test this, VK2/E6E7 vaginal keratinocytes were treated with simvastatin, challenged with purified, recombinant VLY, and loss of membrane integrity and viability was assessed by trypan blue staining and LDH assay. One-way ANOVA with Tukey post-test for comparison of individual groups indicated a significant decrease in VLY-induced LDH release from simvastatin pre-treated cells. Treatment of the cells with either cholesterol or mevalonate (exogenous sources for the cells to assimilate in the absence of biosynthesis) in addition to the simvastatin, reduced the effect, and there was no longer a significant difference relative to untreated cells (p>0.05). Both trypan blue staining and LDH assay indicated that simvastatin pretreatment reduced VLY-mediated toxicity and that this effect was reversed by the addition of cholesterol or mevalonate during the pre-treatment (FIG. 2).

Discussion

This example shows that the mean proportion of *G. vaginalis* was lower in the vaginal microbiomes of women who used statins relative to those of women who were not using statins. The effect was similar regardless of whether the women not using statins reported high or normal serum levels of cholesterol. Statins affect not only serum cholesterol levels, but membrane cholesterol as well. Women taking statins had significantly greater mean proportions of *L. crispatus* and *L. jensenii* relative to non-statin users with normal cholesterol levels and non-statin users with elevated cholesterol levels, respectively. In vitro analysis of membrane permeabilization, as measured by trypan blue staining and LDH release by VLY in vaginal epithelial cells indicated that simvastatin-treatment was protective, demonstrating a mechanism for the reduction in prevalence of *G. vaginalis* in the vaginal environment. Two facts suggest that VLY function may be essential for colonization by *G. vaginalis*. First, VLY is highly conserved in *G. vaginalis*, despite considerable genetic diversity in this species. Second, other CDC's, such as pneumolysin and listeriolysin, play critical roles in colonization and pathogenesis. *G. vaginalis* has been shown to compete with *L. crispatus* for adherence to vaginal epithelial cells, therefore, the increase in the proportion of lactobacilli in women taking statins may be more than a statistical consequence of the decrease in *G. vaginalis*. *G. vaginalis* could also alter the conditions within the vagina in other ways that reduce lactobacilli or compete for resources, including lactic acid. Vaginal epithelial cells store glycogen, and glycogen is strongly associated with colonization by beneficial lactobacilli such as *Lactobacillus* crispatus. VLY can damage vaginal epithelial cells, likely depleting glycogen stores, which would be expected to reduce growth of beneficial lactobacilli and create an environment conducive to the growth of *G. vaginalis* and other BV-associated bacteria. Therefore, interference with VLY function through depletion of plasma membrane cholesterol, can prevent *G. vaginalis* growth and promote the growth of lactobacilli. Alternatively, statin treatment could have a more direct effect, possibly through its anti-inflammatory properties, on the interaction between the host and *L. crispatus* and *L. jensenii*.

In addition to the reduction of cholesterol synthesis, statins mediate a variety of effects on cells. They have anti-inflammatory effects and have been shown to reduce the pathology and severity of a number of infectious and autoimmune diseases. The effect on VLY function may contribute towards the decrease in *G. vaginalis* abundance but that the anti-inflammatory effects also play a role.

AA women are twice as likely to have BV relative to EA women and they are more likely to have a microbiome that falls into the Diversity CST. EA women are more likely to be colonized by *L. crispatus* and have a microbiome that falls into the *L. crispatus* CST. This is clinically relevant because BV-like vaginal microbial profiles are associated with preterm birth, which is more common in AA women, and HIV acquisition. Studies suggest that this disparity cannot be accounted for by differences in demographics, suggesting that genetics plays a role. Interestingly, women using statins exhibited similar CST profiles regardless of ethnicity, suggesting that it could alleviate health disparities associated with the vaginal microbiome. It is known that statins are significantly less effective at reducing LDL in AA women, suggesting that there may be a difference in cholesterol metabolism or in the effect of statins in this group. This suggests that there may be physiological differences in the way that cholesterol is metabolized or trafficked between the two ethnic groups. Clinically, when cholesterol levels are measured, they are measured in serum, not in cellular plasma membranes. Cholesterol levels that would be expected to affect VLY function are the levels in membranes, not in serum. This may explain why ethnic-based differences in cholesterol metabolism have not been previously noted.

Strengths of this study include the use of comprehensive 16S rRNA gene survey and the relatively large sample size; 133 women taking statins, 316 women in the normal cholesterol level control group, and 152 women in the high cholesterol level control group. Because of the variability of the vaginal microbiome amongst women, significant effects of environmental factors are not easily detectable in smaller sample sets. Another strength is the in vitro component, which revealed a potential mechanism for the basis of decreased *G. vaginalis* abundance in women using statins.

CONCLUSION

This study demonstrates that statin use impacts the vaginal microbiome, resulting in an overall improvement in vaginal health by decreasing the abundance of *G. vaginalis* and increasing the abundance of *Lactobacilli*.

While the invention has been described in terms of its several exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of preventing or treating bacterial vaginosis (BV), or a disease or condition that is associated with BV, in a subject in need thereof, comprising
administering to the subject a therapeutically effective amount of a composition comprising i) at least one statin and ii) at least one azetidinone-based cholesterol absorption inhibitor.

2. The method of claim 1, wherein the statin is selected from the group consisting of lovastatin, atorvastatin, rosuvastatin, simvastatin, fluvastatin, pitavastatin, cerivastatin, and pravastatin.

3. The method of claim 1, wherein the azetidinone-based cholesterol absorption inhibitor is a monobactam that does not have anti-bacterial activity.

4. The method of claim 3, wherein the monobactam is ezetimibe.

5. The method of claim 1, wherein administering is performed intravaginally for either or both the at least one statin and the at least one azetidinone-based cholesterol absorption inhibitor.

6. The method of claim 1, wherein the step of administering is performed systemically for at least one of: i) a statin, and ii) an azetidinone-based cholesterol absorption inhibitor that decreases cellular cholesterol.

7. The method of claim 6, wherein the subject does not have high serum cholesterol.

8. The method of claim 1, wherein the disease or condition that is associated with BV is pre-term birth, peripartum infectious morbidity, a sexually transmitted disease, recurrent bacterial vaginosis and vaginal dysbiosis.

9. The method of claim 1, wherein the step of administering is performed by insertion of a vaginal ring comprising the at least one statin and the at least one azetidinone-based cholesterol absorption inhibitor.

10. The method of claim 1, wherein growth of at least one pathogenic bacterial species associated with BV is inhibited.

11. The method of claim 10, wherein said at least one pathogenic bacterial species is selected from the group consisting of *Prevotella, Dialister, Atopobiuin, Gardnerella, Megasphaera, Peptoniphilus, Sneathia, Eggerthella, Aerococcus, Finegoldia,* and *Mobiluncus*.

12. The method of claim 10, wherein said at least one pathogenic bacterial species is *Gardnerella*.

13. The method of claim 1, wherein homeostatic balance between pathogenic species and beneficial species is restored or maintained.

14. The method of claim 13, wherein said beneficial species is at least one *Lactobacillus* selected from the group consisting of *L. crispatus, L. gasseri, L. iners* and *L. jensenii*.

15. The method of claim 1, further comprising the step of inhibiting cholesterol uptake and/or absorption in vaginal epithelial cells.

* * * * *

SEQUENCE LISTING

```
<160> NUMBER OF SEQ ID NOS: 5

<210> SEQ ID NO 1
<211> LENGTH: 56
<212> TYPE: DNA
<213> ORGANISM: Artificial Sequence
<220> FEATURE:
<223> OTHER INFORMATION: Synthetic primer

<400> SEQUENCE: 1
ccatctcatc cctgcgtgtc tccgactcag bbbbbbagag ttygatymtg gctyag        56

<210> SEQ ID NO 2
<211> LENGTH: 56
```

```
<212> TYPE: DNA
<213> ORGANISM: Artificial Sequence
<220> FEATURE:
<223> OTHER INFORMATION: Synthetic primer

<400> SEQUENCE: 2
ccatctcatc cctgcgtgtc tccgactcag bbbbbbagar tttgatcytg gttcag            56

<210> SEQ ID NO 3
<211> LENGTH: 47
<212> TYPE: DNA
<213> ORGANISM: Artificial Sequence
<220> FEATURE:
<223> OTHER INFORMATION: Synthetic primer

<400> SEQUENCE: 3
cctatcccct gtgtgccttg gcagtctcag attaccgcgg ctgctgg                      47

<210> SEQ ID NO 4
<211> LENGTH: 34
<212> TYPE: DNA
<213> ORGANISM: Artificial Sequence
<220> FEATURE:
<223> OTHER INFORMATION: Synthetic primer

<400> SEQUENCE: 4
ggaagggatc cgattcttct gcaaagcctt ctgc                                    34

<210> SEQ ID NO 5
<211> LENGTH: 38
<212> TYPE: DNA
<213> ORGANISM: Artificial Sequence
<220> FEATURE:
<223> OTHER INFORMATION: Synthetic primer

<400> SEQUENCE: 5
ggaagctcga gtcagtcatt ctttacagtt tcagcaac                                38
```